(12) United States Patent
Baid

(10) Patent No.: US 8,959,778 B2
(45) Date of Patent: Feb. 24, 2015

(54) SURGICAL SAFETY SCALPEL

(75) Inventor: Rishi Baid, New Dehli (IN)

(73) Assignee: Poly Medicure Limited, Faridabad (IN)

( * ) Notice: Subject to any disclaimer, the term of this patent is extended or adjusted under 35 U.S.C. 154(b) by 1299 days.

(21) Appl. No.: 12/597,632

(22) PCT Filed: Apr. 28, 2008

(86) PCT No.: PCT/IN2008/000267
§ 371 (c)(1),
(2), (4) Date: Apr. 19, 2010

(87) PCT Pub. No.: WO2008/132762
PCT Pub. Date: Nov. 6, 2008

(65) Prior Publication Data
US 2010/0228274 A1 Sep. 9, 2010

(30) Foreign Application Priority Data
Apr. 26, 2007 (IN) .............................. 917/DEL/2007

(51) Int. Cl.
*A61B 17/32* (2006.01)
*B26B 3/06* (2006.01)
*A61B 17/3213* (2006.01)
*A61B 17/3211* (2006.01)

(52) U.S. Cl.
CPC ... *A61B 17/3213* (2013.01); *A61B 2017/32113* (2013.01)
USPC ............................................. 30/151; 606/167

(58) Field of Classification Search
CPC ........ B26B 3/06; B26B 29/02; B26B 29/025; A61B 17/32; A61B 17/3209; A61B 17/32093; A61B 17/3211; A61B 17/3213
USPC ............. 30/162, 163, 151; 606/167; D24/147
See application file for complete search history.

(56) References Cited

U.S. PATENT DOCUMENTS

| | | | |
|---|---|---|---|
| 3,905,101 A * | 9/1975 | Shepherd | ......................... 30/162 |
| 3,906,626 A * | 9/1975 | Riuli | ............................... 30/162 |
| 4,523,379 A * | 6/1985 | Osterhout et al. | ............... 30/151 |
| 5,123,167 A * | 6/1992 | Kelley | ............................ 30/162 |
| 5,254,128 A | 10/1993 | Mesa | |
| 5,330,492 A * | 7/1994 | Haugen | ......................... 606/167 |
| 5,342,379 A | 8/1994 | Volinsky | |
| 5,417,704 A * | 5/1995 | Wonderley | ..................... 606/167 |
| 5,466,223 A * | 11/1995 | Bressler et al. | ............... 604/110 |

(Continued)

FOREIGN PATENT DOCUMENTS

| WO | 01/74257 A1 | 10/2001 |
|---|---|---|
| WO | WO 2008132762 A1 * | 11/2008 |

OTHER PUBLICATIONS

International Search Report dated Sep. 17, 2008 pertaining to PCT/IN2008/000267.

*Primary Examiner* — Jason Daniel Prone
(74) *Attorney, Agent, or Firm* — IP Attorneys Group

(57) ABSTRACT

A surgical safety scalpel having a handle, a blade fixed at one end of the handle, and a sheath slidably and inseparably attached to the handle. The sheath slides lengthways along the handle alternating between a blocking position in which the sheath covers the blade, and a ready position in which the blade is exposed and the sheath forms part of the grip. An aperture in the sheath and two stoppers on the handle form an interlocking mechanism for maintaining the sheath in the blocking position, and a third stopper on the handle prevents the sheath from sliding off the handle in the ready position.

16 Claims, 4 Drawing Sheets

(56) References Cited

U.S. PATENT DOCUMENTS

| | | | | |
|---|---|---|---|---|
| 5,683,407 A * | 11/1997 | Jolly et al. | | 606/172 |
| 5,752,968 A * | 5/1998 | Jolly et al. | | 606/167 |
| 5,827,309 A * | 10/1998 | Jolly et al. | | 606/167 |
| 5,830,226 A * | 11/1998 | Webb et al. | | 606/167 |
| D470,587 S * | 2/2003 | Howell et al. | | D24/147 |
| D470,938 S * | 2/2003 | Howell et al. | | D24/147 |
| D473,649 S * | 4/2003 | Howell et al. | | D24/147 |
| D475,135 S * | 5/2003 | Howell et al. | | D24/147 |
| 6,626,925 B2 * | 9/2003 | Newman et al. | | 606/167 |
| 6,884,240 B1 * | 4/2005 | Dykes | | 30/162 |
| 7,024,773 B2 * | 4/2006 | Jennings | | 30/151 |
| 7,087,067 B2 * | 8/2006 | Kehr et al. | | 606/167 |
| 7,153,317 B2 * | 12/2006 | Kanodia et al. | | 606/167 |
| 7,346,989 B2 * | 3/2008 | Shi | | 30/151 |
| 7,857,824 B2 * | 12/2010 | Kiehne | | 606/167 |
| 8,114,103 B2 * | 2/2012 | Rasco | | 606/167 |
| 8,156,653 B2 * | 4/2012 | Austria et al. | | 30/162 |
| 8,205,340 B2 * | 6/2012 | Austria et al. | | 30/162 |
| 2003/0093100 A1 | 5/2003 | Robinson | | |
| 2003/0187401 A1 * | 10/2003 | Doyle | | 604/198 |
| 2004/0181247 A1 | 9/2004 | Kehr et al. | | |
| 2004/0236359 A1 * | 11/2004 | Shi | | 606/167 |
| 2007/0060934 A1 | 3/2007 | Rasco | | |
| 2010/0305593 A1 * | 12/2010 | Inzero | | 606/167 |
| 2012/0245610 A1 * | 9/2012 | Hajgato et al. | | 606/167 |

\* cited by examiner

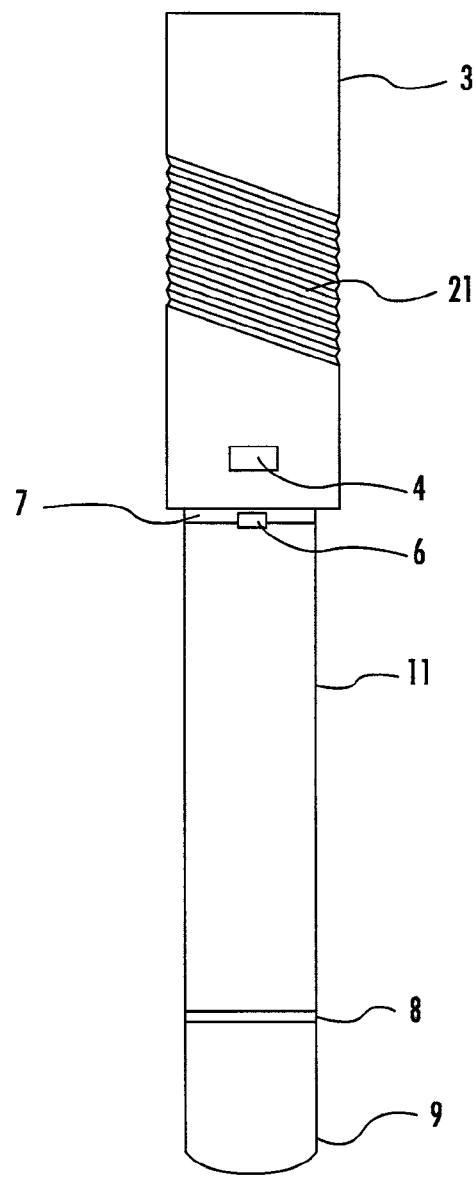
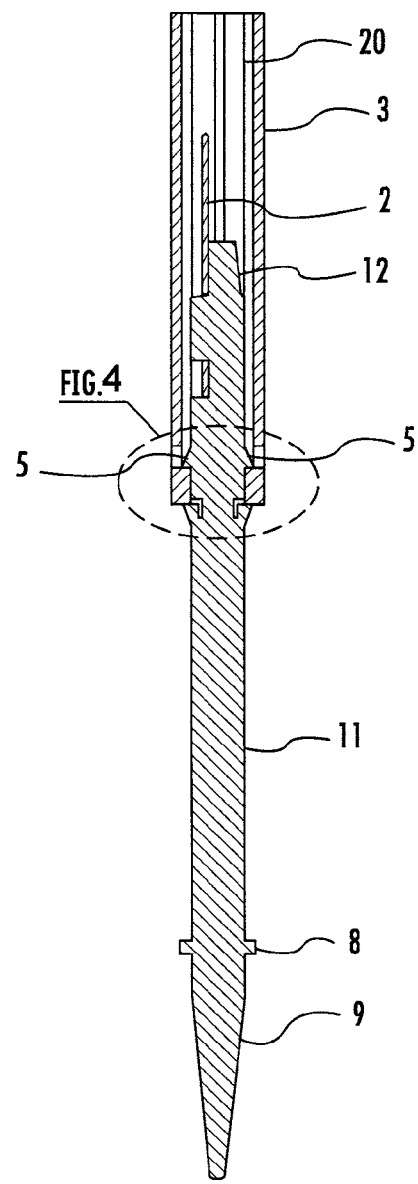
FIG. 2    FIG. 3
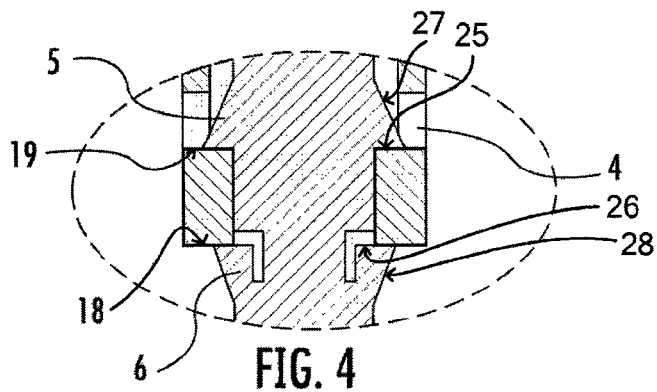
FIG. 4

SURGICAL SAFETY SCALPEL

FIELD OF INVENTION

This invention relates generally to surgical scalpels and, more particularly, to surgical scalpels having sheaths or guards to cover the scalpel blade when not in use.

BACKGROUND OF THE INVENTION

In a world prevalent with AIDS epidemic and Hepatitis B and C epidemics, accidental needle sticks and scalpel cuts have become a major concern to health-care workers. According to a study, the conversion rate for HIV positive needle sticks is 1 in 250 sticks. The conversion rate for scalpel cuts is unknown but according to a study of 10,000 health care workers, it is believed that the conversion rate is higher (as per U.S. Pat. No. 5,342,379). It is well known and understood by healthcare workers that sharp surgical instruments, such as scalpels, have a significant potential for harm to healthcare workers. The rapid handling of these sharp instruments can lead to accidental cuts or puncture wounds during surgery.

Thus, there is an inherent incentive for improvement in scalpel technology that can reduce and more ideally eradicate scalpel cuts to the health care worker. The chance of a healthcare worker contracting a fatal infection or disease because of an accidental scalpel cut comes with a heavy price on society and healthcare. The scalpel has not had many basic changes made in the past 100 years other than disposable blades and micro-surgical sizes.

Typically, most scalpel cuts or stabs occur in specific situations, such as a surgery. One occasion is at the time of passing a used scalpel to a scrub nurse. Another is when a surgeon swabs a bleeder and accidentally stabs himself (when he forgets that the scalpel is in his other hand). Trauma cases are another high risk situation in which an accidental laceration can occur because there many people simultaneously working on these cases and people are rushing to perform their tasks. Yet another case of accidental stabs is that if the blade sheath is lost or misplaced, the scalpel becomes dangerous for practically anyone and everyone in the proximity of the exposed scalpel blade. Another instance is during the disposal of medical waste, stabbing may occur because of accidental removal of the blade sheath. During the course of a surgery, the healthcare worker will usually remove the sheath and give the exposed scalpel blade to the doctor. Similarly after completion of the use of the scalpel, the surgeon may hand the exposed scalpel blade to the healthcare worker for covering. This process results in loss of time and may cause accidental stabbing of the healthcare worker or the surgeon. During waste disposal, the disposer is not always careful in handling the waste and may handle the waste roughly, which may result in removal of the sheath (if not already detached) and cause stabbing. This could also lead to spread of infection in the general public. Thus, there is a need to protect the healthcare workers from accidental scalpel stabs To address this issue, in recent years, scalpels with disposable blade portions have been made. In this type of scalpel, the blade component is detachable from the handle component and disposed of by deposit in a special container. It will be appreciated, however, that such disposal of blades still presents a hazard to the individual who must detach and transfer the blade component.

Similarly, blade sheaths have been developed to cover the scalpel blade when the scalpel is not in use. While early blade sheaths did help reduce the potential for accidental cuts or puncture wounds, there were some problem areas. For example, safety scalpels are known that have a retractable external sheath, but they require two hands to operate. Some of the blade sheaths are awkward to operate. Others include complex mechanical mechanisms to move the sheath, which mechanisms could be prone to mechanical failure.

Attempts have been made to sheath the blade in the knife itself by providing a hollow handle component with a slidable blade therein. Basically, these instruments employ the handle component as a sheath for the blade component when not in use. Typically, such sheathable blade assemblies are not contemplated for disposal after a single use. Furthermore, such cutting instruments do not provide a positive means for preventing the unsheathing of the blade portion by a careless handler when disposal of the blade is desired.

Therefore, it is an object of the invention to provide a surgical scalpel assembly that reduces the complexity of prior known scalpel devices and which also provides additional safety and manufacturing benefits over known scalpel systems.

SUMMARY OF THE INVENTION

One embodiment of this invention is a surgical safety scalpel comprising a scalpel handle with a provision to removably attach a disposable scalpel blade at one end, and a longitudinally moveable blade sheath on the handle. The sheath is securely attached to the scalpel handle and entirely covers the scalpel blade in a closed and protective state or blocking position. The sheath can be made to slide towards the tail of the scalpel handle and lock on the central part of the scalpel handle when the scalpel blade is in its exposed state or ready position. The sheath is a hollow body that locks on the scalpel handle by apertures provided on the distal end of the sheath, which apertures interlock with the stoppers at the proximal end of the scalpel handle near the stem of scalpel blade when the sheath is in the blocking position. The first stopper prevents the sheath from sliding beyond the blocking position and detaching from the handle. When the sheath is in this blocking position, the second stopper prevents the sheath from sliding down over the handle by radially exerting force on to a distal end of the sheath. The second stopper is placed inside a recess on the handle and projects outwards. The second stopper has a flexible nature and exerts outward force. When the sheath is in blocking position the outward exerted force keeps the sheath in such blocking position. When the sheath is in the ready position the tail stopper prevents the sheath from sliding off the distal end of the handle. The aperture may have a small projection inside the aperture extending parallel or substantially parallel to the handle, which projection interlocks with the first stopper in the blocking position. The sheath has a grip on the sheath surface to assist in transitioning the sheath from ready position to blocking position over the blade and provide traction for the user.

The scalpel blade can be simply covered with the sheath by using one hand and more particularly one digit of the hand holding the scalpel to slide the sheath over the blade. The scalpel blade is covered by the sheath with a shift of the thumb. This covering can be affected after each cut has been made. The sheathing is a smooth single hand operation without any risk of cutting oneself.

An object and advantage of the invention is to provide a safety sheath for the scalpel blade wherein the sheath forms an integral and inseparable part of the body of the scalpel.

Another object and advantage of this invention is that the sheath does not need to be removed from the scalpel blade during surgery, Yet another object and advantage of this invention is the locking of the sheath on the body of the scalpel so that the sheath cannot be removed from the scalpel body easily or accidentally. A deliberate attempt and a lot of force will be required to remove the sheath from the body of the scalpel.

BRIEF DESCRIPTION OF THE DRAWINGS

FIG. 2 is a view of one embodiment of the present invention with the sheath in the blocking position.

FIG. 3 is a cross-sectional view of one embodiment of the present invention with the sheath in the blocking position.

FIG. 4 is a detail view of the interlocking mechanism with the sheath in the blocking position.

DETAILED DESCRIPTION OF THE INVENTION

Figure 1:
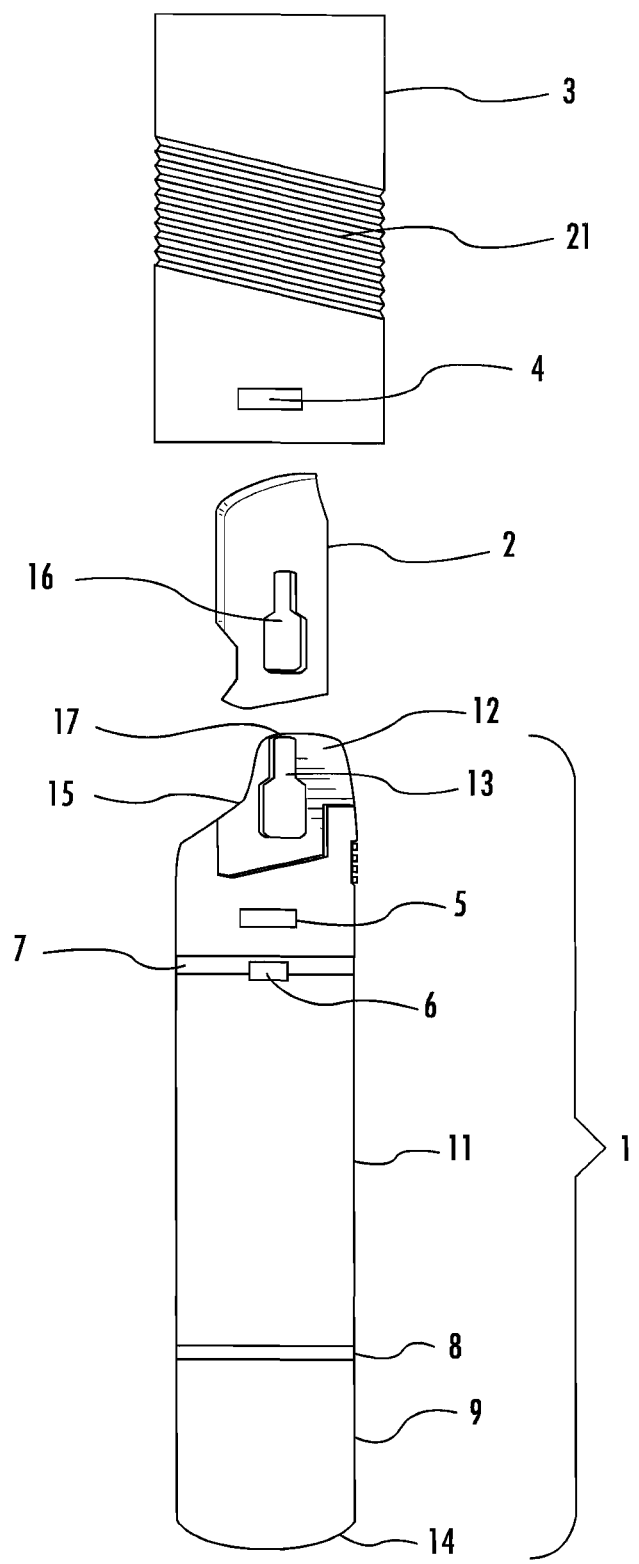
FIG. 1 is an exploded view of one embodiment of the blade and sheath of the present invention together with a scalpel handle.

Referring to FIG. 1, there is shown an exploded view of one embodiment of the scalpel handle, blade, and sheath of the instant invention.

In this embodiment, the scalpel handle 1 is of conventional shape and configuration having a distal end 14 and a proximal end 12. This handle is made of plastic, stainless steel or other suitable material and of such nature that can withstand all types of sterilization ranging from chemical to heat (both dry or wet) or any other sterilization. Typically, the distal end 14 on the tail 9 is relatively thin while the middle portion 11 is somewhat thicker. The proximal end 12 of the scalpel handle generally takes the configuration of an extended nose which is relatively narrow and includes a projection 13 on at least one surface thereof. The projection 13 incorporates a groove 17 for receiving a blade 2.

The scalpel handle 1 can taper in width towards the distal end 14 near the tail 9. On at least one of the surfaces of the handle 1, the scalpel handle includes a plurality of surface features including stoppers in the nature of ridges, protrusions, buttons, and combinations thereof; and cavities in the nature of slots, recesses, grooves and combinations thereof, certain protrusions and cavities configured to engage complementary elements on a sheath. In one exemplary embodiment shown in FIGS. 1-8, the protrusions include a first stopper 5 in the form of a protrusion, a second stopper 6 in the form of a flexible button, and a tail stopper 8 in the form of a ridge extending across the width of the handle 1. The cavities on this embodiment include a recess 7 undercutting second stopper 6 to provide means for the second stopper 6 to flex. In other embodiments, the structures of the first, second, and third stoppers may be independently selected from ridges, protrusions, or buttons.

Typically, the distal end 14 of the handle 1 is somewhat rounded for convenience. In addition, a shoulder 15 can be provided at the end of the scalpel adjacent to the proximal end 12.

The sheath 3 is also disclosed, having a distal portion which slides along the handle 1 and a proximal portion which extends beyond the proximal end 12 of the handle 1 to cover the blade 2. While not necessarily limited thereto, the sheath 3 is typically formed of a plastic material such as a conventional polymer material including but not limited to polystyrene, polycarbonate, polyurethane, polyethylene, phenol-formaldehyde resins, polybutylene and the like. The sheath further comprises a base surface 18 configured to engage the second stopper 6 when the sheath is in the blocking position, and to engage the tail stopper 8 when the sheath is in the ready position.

As shown in FIG. 1, a plurality of substantially parallel, transverse strips 21 are provided across the outer surface of the sheath 3. These strips (or ridges) can be raised or depressed areas in the body of the sheath 3. The strips 21 provide additional traction or gripping surfaces for the user of the sheath 3.

An aperture 4 having a square shape is provided through the proximal portion of the sheath 3. The aperture 4 and the base surface of the sheath are shaped to correspond, cooperate and lock with first stopper 5 and second stopper 6 while the sheath is enclosing the scalpel blade 2. The second stopper 6 is provided a short distance from the first stopper 5 in a direction along handle 1 towards the distal end 14. The second stopper 6 limits the movement of the sheath 3 relative to the scalpel handle 1 when in blocking position.

A representative blade 2 is shown. The shape of the cutting edge of the blade and so forth are representative only. It is well known that there are many sizes, shapes and styles of scalpel blades. The invention described herein is intended to cooperate with virtually any blade shape.

Typically, the blade 2 includes an opening 16 which is configured to cooperate with and engage the projection 13 of the handle 1. Typically, the projection 13 is inserted into the larger portion of the opening 16 and slid forward to engage the smaller end of the opening 16 in a groove 17 in the projection 13. When the blade 2 is to be attached to handle 1, the proximal end 12 of the handle is exposed by sliding the sheath 3 down on to the middle portion 11 of the handle. The projection 13 of the handle 1 is inserted into and mates with the opening 16 in the blade in conventional fashion. The scalpel is now in armed and ready position.

To disarm the scalpel without touching the exposed blade 2, the sheath 3 that is resting on the middle portion 11 of the handle 1 is pushed smoothly from the middle portion 11 over the blade 2 until the sheath 3 completely covers the blade 2. The forward motion of the sheath 3 is stopped by the engagement of the aperture 4 with first stopper 5 and the base of the sheath 3 with second stopper 6. The sheath 3 is now locked over the blade 2 in the blocking position, and the blocked scalpel can be kept safely for future use by the healthcare worker.

In FIG. 2, the middle portion 11 is shown along with the position thereof relative to the sheath 3 when the sheath 3 is in the blocking position. The blade is stored within the sheath 3 for safe and secure handling thereof without a danger of harm to the handler of the blade.

Referring now to FIG. 3, there is shown by cross section the condition wherein the blade 2 is fully mounted onto the proximal end 12 of the handle 1. The sheath 3 covers the blade 2 and a portion of the scalpel handle 1.

Figure 5:
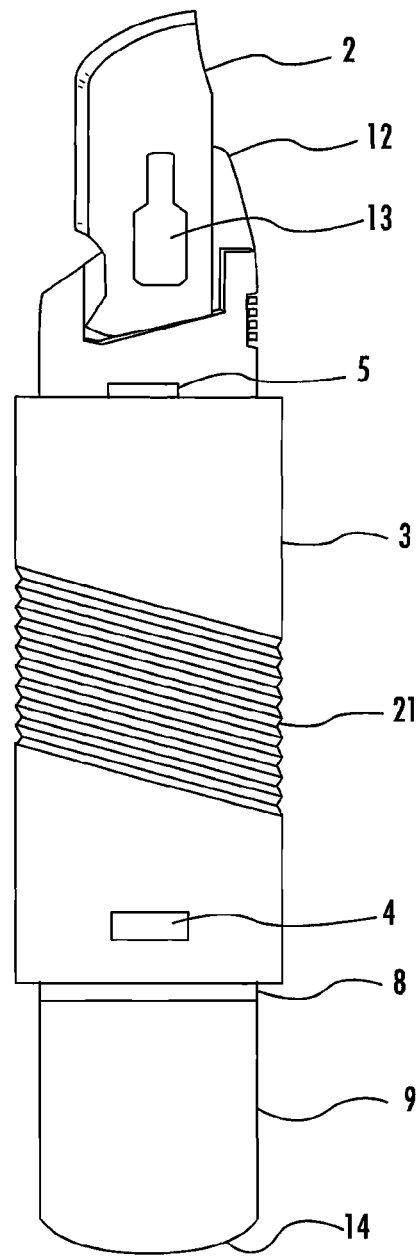
FIG. 5 is a view of one embodiment of the present invention, with the sheath in the ready position and the blade exposed.

When it is desired to use the blade, the sheath 3 is withdrawn from the blade 2 by sliding it along the handle 1 to the ready position shown in FIG. 5. When the cutting procedure is concluded, the sheath 3 is repositioned over the blade 2 by sliding the sheath 3 back over the blade 2 into the blocking position shown in FIG. 2. When the sheath 3 is returned to the position shown in FIG. 2, the blade 2 is covered and the scalpel device can be handled in any appropriate fashion without fear of an accidental cut therefrom.

FIG. 4 shows a detail view of the locking mechanism of the sheath 3 with the scalpel handle 1. First stopper 5 engages with the distal portion 19 of the aperture 4, thereby stopping the sheath 3 from slipping past the scalpel blade 2 after the sheath has completely enclosed and secured the scalpel blade 2. So that the sheath does not slide down the handle 1 and continues to remain in blocking position, the second stopper 6 prevents the sheath 3 from sliding down by engaging with the base 18 of the sheath 3. Therefore, the aperture 4, the first stopper 5, second stopper 6 and the base 18 of the sheath 3 form an interlocking mechanism to retain the sheath 3 in the blocking position. As can be seen in FIG. 4, when the button forming the second stopper 6 is depressed, the base of the sheath can slide over the second stopper while the back edge of the aperture 4 slides over the sloped back surface of first stopper 5.

Figure 7:
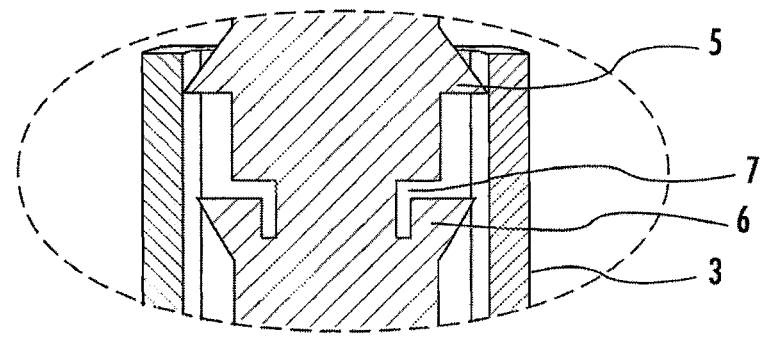
FIG. 7 is a detail view of an embodiment of the present invention when the sheath is in the ready position.

The second stopper 6 is made of a flexible material. The second stopper 6 can obviously be made of any material that has flexible properties. This second stopper 6 acts as a spring. During ready position of the sheath 3, the second stopper 6 has radial tension typical of a spring that exerts pressure against the opposing inner walls 20 of the sheath. When the sheath 3 is activated and eventually comes to rest in the blocking position, the second stopper 6 is freed from the inner wall 20 of the sheath 3 and the spring action or the radial tension causes the second stopper 6 to spring outwards. This outward spring movement of second stopper 6 results in providing a retaining means for the sheath 3 to remain in the blocking position. The detail section view in FIG. 4 best explains the working of this second stopper 6. In the embodiment depicted, it can be seen that first stopper 5 has an inner face 25 and an outer face 27, and second stopper 6 has an inner face 26 and an outer face 28. In this embodiment, the first stopper inner face 25 and the second stopper inner face 26 are opposite each other and substantially perpendicular to a longitudinal axis of handle 1 to positively engage the distal portion 19 of the aperture 4 and the base surface 18 of the sheath 3 respectively, as shown in FIG. 4. It can also be seen that the first stopper outer face 27 and the second stopper outer face 28 each slope down to the handle 1, permitting the sheath to slide when the interlocking mechanism is disengaged, but exert radial outward pressure against the inner walls 20 of the sheath 3 as shown in FIG. 7. It can also be seen from FIG. 4 and FIG. 7 that stopper 6 is given flexibility by undercutting with recess 7.

Figure 6:
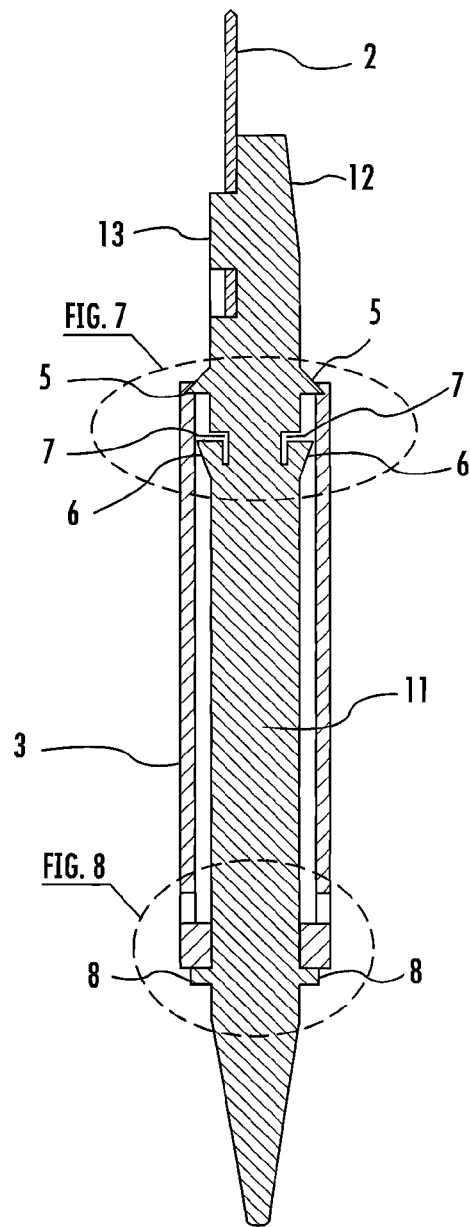
FIG. 6 is a cross-sectional view of one embodiment of the present invention in ready position.

Referring now collectively to FIG. 5 and FIG. 6 there is shown a view of the sheath 3 and blade 2 mounted on the proximal end 12 of the handle 1. This view is to explain the construction and working of the scalpel when sheath 3 is in ready position.

To attain the ready position shown in FIG. 5 with the sheath 3 retracted to expose the blade 2 for any suitable cutting purposes or when it is desired to remove the blade 2 from the handle 1, the sheath 3 is moved away from the blade 2 and onto the middle portion 11 of the handle 1. It is understood that the blade 2 is securely fastened to the scalpel handle 1 as described above. The sheath 3 is withdrawn along the handle 1 by exerting pressure on the gripping surface comprising strips 21. Typically, the sheath 3 is operated by depressing second stopper 6, pulling on the gripping surface using the thumb and index finger or any other finger, and pushing the handle 1 through the sheath 3, exposing the blade 2.

Figure 8:
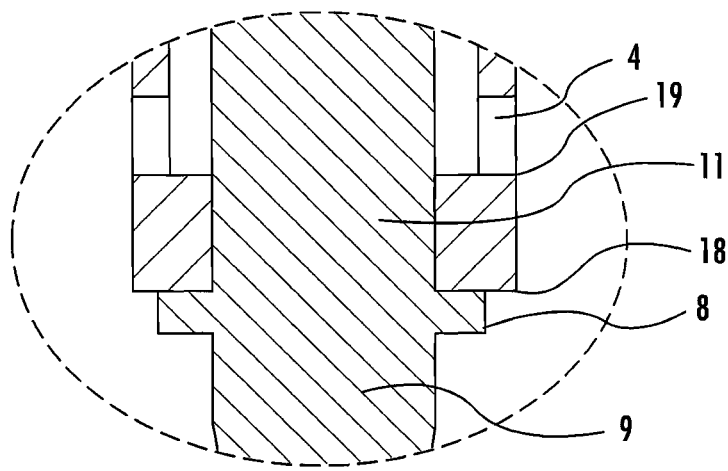
FIG. 8 is a detail view of an embodiment of the present invention when the sheath is in the ready position.
Figure 9:
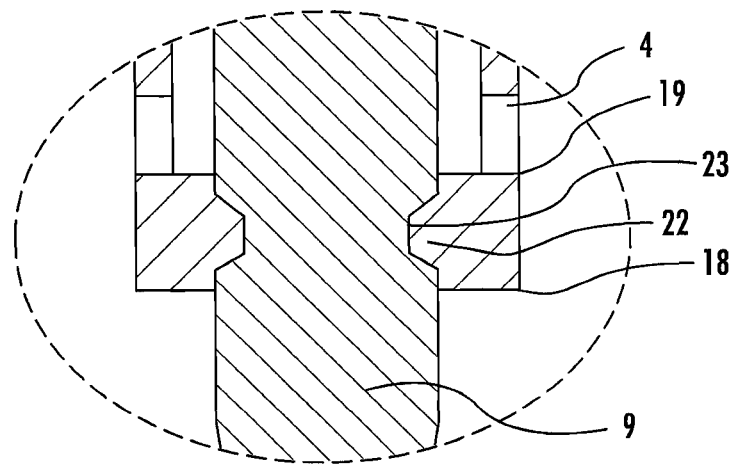
FIG. 9 is a detail view of an embodiment of the present invention when the sheath is in the ready position.

It can be seen that in the ready position shown in FIG. 5, the blade 2 is attached to the handle 1 but is completely exposed and ready for use or already used, as the situation may be. The sheath 3 is in the ready position and is resting on the middle portion 11 of the scalpel handle 1. The sheath 3 is comfortably mounted on the middle portion 11 of the handle 1 in such a position that the sheath 3 covers a part of the middle portion 11 of the handle 1, providing a gripping or traction surface for the user. So that the sheath 3 does not slide off the distal end 14 of the handle 1, the handle is provided with tail stopper 8 on the end proximal to the rounded distal end 14 of the handle. In the exemplary embodiment shown in FIGS. 5 and 6, the tail stopper 8 is in the form of a ridge projecting from the surface of the handle 1 which engages the base of sheath 3. FIG. 8 shows a detail view of the sheath 3 in the ready position engaged with the tail stopper 8. In a second embodiment, as shown in FIG. 9, the tail stopper 8 is in the form of a recess 23 in the surface of the handle 1 which interacts and mates with projections 22 from inside the inner walls 20 of the sheath 3.

The ready position of the sheath 3 enables the scalpel with blade 2 to be used easily and effectively without any requirement to remove the sheath 3 from the handle 1. From this position, sheath 3 can be slid into blocking position quite easily at the end of the cutting procedure.

To unsheathe the blade 2, the second stopper 6 is depressed and sheath 3 can be pushed back and downwards over the body of the handle 1. In this case, the force exerted on the sheath is sufficient to override the restraint caused by the second stopper 6, the flexibility of the sheath allowing it to ride over the first stopper 5. It can be seen from FIGS. 6 and 7 that the first stopper 5 extends slightly beyond the space allowed by the inner wall of the sheath; it can easily be understood, however, that very slightly flexibility in the sheath 3 allows it to ride over first stopper 5, giving a more positive interlock when first stopper 5 engages aperture 4. In the preferred embodiment, the second stopper 6 is made of flexible material and has radial tension directed outwardly against the inner walls 20 of sheath 3 (see FIG. 7). This arrangement provides additional security to prevent the sheath 3 from inadvertently sliding back over and covering the blade during a cutting procedure.

The length of the sheath 3 is such that it just covers the first stopper 5 while resting on tail stopper 8 in the ready position. Furthermore, the length of the sheath 3 is such that it completely covers the blade 2 when extended into the blocking position. Such a construction assists in the preferred working of the sheath 3 but does not necessarily mean that other combinations are not possible.

FIG. 7 shows the detailed cross-sectional view of the proximal end of sheath 3 in ready position. This figure shows the detail of second stopper 6 and the radial tension extending outwards into the inner wall 20 of the sheath 3.

Thus, there is shown and described a unique design and concept of a scalpel blade cover. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

I claim:

1. A surgical safety scalpel comprising a blade, a sheath, and a handle, wherein the blade is fixed at one end to an extended nose on the handle, and wherein said sheath is longitudinally, slidably and inseparably mounted on said handle; said sheath further comprising a first surface, a second surface and two side surfaces connecting the first and second surfaces, said sheath having a base surface defined by an edge of each of the first, second, and side surfaces and having an opening; said sheath further comprising an aperture through at least one of the surfaces of said sheath; a first stopper and a second stopper mounted on the handle, a face of said second stopper aligned opposite to a face of said first stopper, wherein said aperture of the sheath is in contact with the face of the first stopper and the base surface of said sheath is stopped by the face of the second stopper when the sheath is in a blocking position, covering said blade, and wherein the base of said sheath is stopped by a third stopper on or near a tail of said handle, preventing said sheath from sliding off of the handle when the sheath is in a ready position, wherein said first stopper also engages with said sheath to resist a sliding movement of said sheath towards said blade when the sheath is in the ready position.

2. The surgical safety scalpel as claimed in claim 1, wherein the second stopper mounted on a portion of the handle distal to the first stopper and on a same side of the handle as the first stopper thereby defining the opposite alignment of the stopper faces and wherein said second stopper is configured to resist movement of the sheath from out of the blocking position when the blade is not in use.

3. The surgical safety scalpel of claim 2 in which said second stopper has a radial tension exerting outwards on an inner surface of the sheath when in the ready position.

4. The surgical safety scalpel of claim 1 in which said first stopper defines a first face proximal to the blade having a slope extended outward from the handle in a direction distal to the blade and towards the tail of the handle, and a second face distal to the blade extending substantially perpendicular to a longitudinal axis of the handle.

5. The surgical safety scalpel as claimed in claim 1 wherein said third stopper is on a proximal end of the tail of the handle.

6. The surgical safety scalpel of claim 5 in which said third stopper is in the form of a projection from a surface of the handle.

7. The surgical safety scalpel of claim 5 in which the third stopper is in the form of a recess in the handle that mates with a projection inside the sheath wall.

8. The surgical safety scalpel of claim 1 in which said sheath further comprises a grip on at least one of the surfaces of the sheath to facilitate holding by the user.

9. A surgical safety scalpel comprising a handle and a sheath mounted on the handle, said sheath further comprising a first surface, a second surface, and two side surfaces connecting the first and second surfaces, and a base surface defined by an edge of each of the first, second, and side surfaces, the handle further comprising a first stopper which engages an aperture in said sheath, a second stopper having a face extending substantially perpendicular to a longitudinal axis of the handle which engages the base surface of said sheath, and a third stopper; wherein the sheath occupies a first position wherein the first stopper is engaged in the aperture and the face of the second stopper is engaged with the base surface of the sheath, and a second position wherein the third stopper is engaged with the base of the sheath; and wherein the sheath is movable from the first position to the second position and from the second position to the first position.

10. The surgical safety scalpel of claim 9 wherein said first stopper exerts force against an inner wall of said sheath when said sheath is in the second position.

11. The surgical safety scalpel of claim 9 further comprising a blade fixed at an end of the handle, wherein the first position is a blocking position in which said sheath surrounds said blade.

12. The surgical safety scalpel of claim 11 wherein the second position is a ready position in which the blade is accessible.

13. The surgical safety scalpel of claim 12 wherein said second stopper is configured to resist movement of the sheath out of the blocking position when the blade is not in use.

14. A surgical safety scalpel, comprising:
a handle having a distal end and a proximal end;
a blade attached to said proximal end;
a sheath having a first opening, a second opening, a hollow body extending from the first opening to the second opening, and a base surface defined by an outermost surface of the hollow body surrounding the first opening, said sheath affixed to said handle;
an aperture in a wall of said sheath;
a first stopper and a second stopper attached to said handle, wherein said second stopper further comprises a face substantially perpendicular to a longitudinal axis of said handle;
wherein said sheath occupies a first position in which the distal end of the handle protrudes from the first opening and the blade is between the first and second opening, said sheath occupies a second position in which the distal end of the handle protrudes from the first opening and the blade protrudes from the second opening, and said sheath can be repeatedly moved from said first position to said second position and from said second position to said first position; and
wherein said first stopper is in contact with said aperture when the sheath occupies the first position, and the face of said second stopper is in contact with said base surface when the sheath occupies the first position.

15. The surgical safety scalpel of claim 14 wherein the sheath is permanently and slidably affixed to said handle.

16. The surgical safety scalpel of claim 14, wherein the hollow body substantially covers the blade when the sheath is in the first position, and exposes the blade when the sheath is in the second position; and wherein the sheath remains affixed to said handle while sliding from the first position to the second position and from the second position to the first position.

* * * * *